(12) United States Patent
Sanderberg et al.

(10) Patent No.: US 10,183,911 B2
(45) Date of Patent: Jan. 22, 2019

(54) PROCESS FOR THE PREPARATION OF A POLYUNSATURATED KETONE COMPOUND

(71) Applicant: Avexxin AS, Trondheim (NO)

(72) Inventors: Marcel Sanderberg, Oslo (NO); Inger-Reidun Aukrust, Oslo (NO)

(73) Assignee: Avexxin AS, Trondheim (NO)

( * ) Notice: Subject to any disclaimer, the term of this patent is extended or adjusted under 35 U.S.C. 154(b) by 0 days.

(21) Appl. No.: 15/545,435

(22) PCT Filed: Jan. 25, 2016

(86) PCT No.: PCT/EP2016/051456
§ 371 (c)(1),
(2) Date: Jul. 21, 2017

(87) PCT Pub. No.: WO2016/116634
PCT Pub. Date: Jul. 28, 2016

(65) Prior Publication Data
US 2018/0009745 A1    Jan. 11, 2018

(30) Foreign Application Priority Data
Jan. 23, 2015 (GB) .................... 1501144.8

(51) Int. Cl.
| | | |
|---|---|---|
| C07C 319/14 | (2006.01) | |
| C07C 319/28 | (2006.01) | |
| C07C 319/02 | (2006.01) | |
| C07C 327/22 | (2006.01) | |
| C07C 303/28 | (2006.01) | |

(52) U.S. Cl.
CPC .......... *C07C 319/14* (2013.01); *C07C 303/28* (2013.01); *C07C 319/02* (2013.01); *C07C 319/28* (2013.01); *C07C 327/22* (2013.01)

(58) Field of Classification Search
CPC ... C07C 303/28; C07C 319/02; C07C 319/14; C07C 327/22; C07C 319/28
See application file for complete search history.

(56) References Cited

U.S. PATENT DOCUMENTS

| | | | |
|---|---|---|---|
| 7,687,543 B2 | 3/2010 | Johansen et al. | |
| 8,524,776 B2 | 9/2013 | Johansen et al. | |
| 8,796,251 B2 | 8/2014 | Johansen et al. | |
| 8,865,768 B2 | 10/2014 | Johansen et al. | |
| 9,187,396 B2 | 11/2015 | Johansen et al. | |
| 2012/0277437 A1* | 11/2012 | Connon .................. | C07B 57/00 546/134 |
| 2013/0245127 A1 | 9/2013 | Feuerherm et al. | |
| 2015/0202165 A1 | 7/2015 | Johansen et al. | |
| 2015/0290144 A1 | 10/2015 | Johansen | |

FOREIGN PATENT DOCUMENTS

| | | | |
|---|---|---|---|
| DE | 10021772 A1 * | 3/2001 | ........... G01N 31/005 |
| EP | 0418680 A2 | 3/1991 | |
| WO | 02/10991 A2 | 12/2002 | |
| WO | 2010 139482 A1 | 12/2010 | |
| WO | 2012028688 A1 | 3/2012 | |
| WO | 2012/140194 A2 | 10/2012 | |
| WO | 2014/082960 A1 | 6/2014 | |
| WO | 2015/011206 A1 | 1/2015 | |
| WO | 2015/181135 A1 | 12/2015 | |

OTHER PUBLICATIONS

SK ("Reduction with metal hydrides", https://en.chem-station.com., Apr. 2014, 7 pages), Mengele et al. ("Effects of Oxygen and Antioxidants on the cis-trans-Isomerization of Unsaturated Fatty Acids Caused by Thiyl Radicals", Moscow University Chemistry Bulletin, 2010, vol. 65, No. 3, pp. 210-211).*
C. Ferreri et al. "Trans Fatty Acids in Membranes: The Free Radical Path", (2007) Mol. Biotech. 37:19-25.
Mengele, E.A et al. "Effects of Oxygen and Antioxidants on the cis-trans-Isomerization of Unsaturated Fatty Acids Caused by Thiyl Radicals", (2010) Mos. Univ. Chemistry Bull 65: 210-211.
Klein, E and N. Weber "In Vitro Testfor the Effectiveness of Antioxidants as Inhibitors of Thiyl Radical-Induced Reactions with Unsaturated Fatty Acids", (2001) J. Agric. Food Chem. 49: 1224-1227.
Huwiler, A et al. "The w3-polyunsaturated fatty acid derivatives AVX001 and AVX002 directly inhibit cytosolic phospholipase A2 and suppress PGE2 formation in mesangial cells", (2012) Br. J. Pharm. 167: 1691-1701.
Holmeide, A and L. Skattebol, "Syntheses of some polyunsaturated trifluoromethyl ketones as potential phospholipase A2 inhibitors", (2000) J. Chem. Soc. Perkin Trans. 1: 2271-2276.

(Continued)

*Primary Examiner* — Rosalynd A Keys
(74) *Attorney, Agent, or Firm* — McCarter & English, LLP; Steven G. Davis

(57) ABSTRACT

A process for the preparation of a polyunsaturated thiol comprising:

(1) reacting a polyunsaturated alcohol in the presence of a compound of formula $R_2$—$SO_2Hal$ wherein $R_2$ is a $C_{1-20}$ hydrocarbyl group, such an $C_{1-10}$ alkyl group, to form a polyunsaturated sulphonyl ester;

(2) converting the polyunsaturated sulphonyl ester to a polyunsaturated thioester by reacting with an anion of formula $^-SC(=O)R_4$ wherein $R_4$ is a $C_{1-20}$ hydrocarbyl group;

(3) converting the polyunsaturated thioester to form a polyunsaturated thiol optionally in the presence of an antioxidant, e.g. using a metal carbonate.

(4) reacting said polyunsaturated thiol with a compound $(LG)R^3COX$ wherein X is an electron withdrawing group and $R^3$ is an alkylene group carrying a leaving group (LG), such as $LG$-$CH_2$— forming

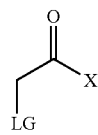

where X is an electron withdrawing group and LG is a leaving group; optionally in the presence of an antioxidant, so as to form a polyunsaturated ketone compound.

24 Claims, No Drawings

(56) References Cited

OTHER PUBLICATIONS

But, T and P. Toy, "The Mitsunobu Reaction: Origin, Mechanism, Improvements, and Applications", (2007) Chem. Asian J. 2: 1340-1355.
Swamy, K.C et al., Mitsunobu and Related Reactions: Advances and Applications (2009) Chem. Rev. 109: 2551-2651.
Chatgilialoglu, C et al., "Geometrical isomerism of Monounsaturated Fatty Acids: Thiyl Radical Catalysis and Influence of Antioxidant Vitamins", (2002) Free Rrad. Biology & Medicine, 33: 1681-1692.
Hung, W-L, et al., "Inhibitor Activity of Natural Occuring Antioxidants on Thiyl Radical-Induced trans-Arachidonic Acid Formation", (2011) J. Agric. Food Chem. 1968-1973.
A. Narian Rai, et al.,"Sphingolipid Synthesis via Olefin Cross Metathesis: Preparation of a Differentially Protected Building Block and Application to the Synthesis of D-erythro-Ceramide", Organic Letters, vol. 6, No. 17, pp. 2861-2863 (2004).
International Search Report cited in PCT/EP2016/051456, dated Apr. 4, 2016.
F. D. Gunstone, et al., "Fatty Acids, part 42—The Preparation and Properties of Methyl Monomercaptostearates, Some Related Thiols, and Some Methyl Epithiostearates", Chemistry and Physics of Lipids, vol. 13, 1974.
Intellectual Property Office Search Report in GB1501144.8, dated Oct. 29, 2015.

* cited by examiner

PROCESS FOR THE PREPARATION OF A POLYUNSATURATED KETONE COMPOUND

This application is a National Phase application filed under 35 U.S.C. § 371 of PCT International Application No. PCT/EP2016/051456 with an International Filing Date of Jan. 25, 2016, which claims under 35 U.S.C. § 119(a) the benefit of Great Britain Application No. 1501144.8, filed Jan. 23, 2015, the entire contents of which are incorporated herein by reference.

FIELD OF THE INVENTION

This invention relates to a method of making a polyunsaturated thiol compound and subsequent conversion of that thiol compound into a polyunsaturated ketone. In particular, the invention relates to the conversion of a polyunsaturated alcohol to a polyunsaturated thiol compound allowing conversion of that polyunsaturated thiol to a polyunsaturated ketone. The invention avoids unwanted oxidation reactions and cis/trans isomerism reactions are substantially reduced or eliminated during the synthesis. We also achieve a very high overall yield.

BACKGROUND

Many biologically active polyunsaturated fatty acids have one or more carbon-carbon double bonds in the cis configuration. Free radicals have been reported to support isomerization of these bonds to a less desirable trans configuration. Cis/trans isomerization can adversely effect polyunsaturated compounds intended for pharmaceutical use, for example, by reducing biological activity, and/or complicating synthesis. See, for example, C. Ferreri et al. (2007) *Mol. Biotech.* 37:19; Chatgilialoglu, C et al. (2002) *Free Rrad. Biology & Medicine,* 33: 1681; and WO 2002/100991.

Some, but not all, free radicals have been reported to support cis/trans isomerism of particular polyunsaturated compounds. It is believed that the kinetics of radical-mediated oxidation depend on several parameters including the chemical nature of the unsaturated compound to be made, temperature, pH, presence or absence of light, oxygen, etc. Free radicals have been reported to occur naturally in the environment or as unwanted by-products that are produced from certain chemical reactions. See, for example, Mengele, E. A et al. (2010) *Mos. Univ. Chemistry Bull* 65: 210.

There have been attempts to reduce oxidation and cis/trans isomerism of carbon-carbon double bonds. In one approach, an antioxidant such as octyl gallate, ascorbic acid, a polyphenol, mercaptoethanol, beta-carotene, or 2,6,-di-tert-butyl-4-methylphenol (BHT), for example, is added to reduce unwanted oxidation reactions. See Mengele, E. A, ibid; Klein, E and N. Weber (2001) *J. Agric. Food Chem.* 49: 1224; and Hung, W-L, et al. (2011) *J. Agric. Food Chem.* 1968.

There have been reports that certain polyunsaturated trifluoromethyl ketone compounds have useful biological activities. See, for example, U.S. Pat. No. 7,687,543; Huwiler, A et al. (2012) *Br. J. Pharm.* 167: 1691.

Methods for preparing particular polyunsaturated ketones have been disclosed. In one method disclosing the synthesis of particular polyunsaturated trifluoromethyl ketones, a Mitsunobu-type reaction was used to transform an alcohol to the corresponding thioester. Further chemical reactions were said to produce the polyunsaturated trifluoromethyl ketone (compound 18 therein) in 71% yield. See Holmeide, A and L. Skattebol (2000) *J. Chem. Soc. Perkin Trans.* 1: 2271. There are however concerns that this process can lead to double bond racemisation and unwanted oxidation reactions.

There is general recognition that a compound intended for pharmaceutical use should be produced in high yield, e.g. 70% or more. Less than satisfactory yields can be associated with unwanted side products. These can be costly or difficult to remove from the main product (API), thereby making further pharmaceutical development difficult. Additionally, regulatory agencies often require a detailed analysis of side products in compounds intended for pharmaceutical use. This requirement can make scale-up costs prohibitive.

The present inventors seek a process for the manufacture of a polyunsaturated thiol and eventually a corresponding polyunsaturated ketone that produces, after suitable purification, a pharmaceutical grade compound with minimal oxidation and cis/trans isomerization by products. After extensive synthetic work, the inventors have determined that a particular process as claimed herein offers an ideal route to the compounds of the invention as the process operates with minimal oxidation and cis/trans isomerization by products. The process described herein not only achieves very high purity but achieves very high yield. It can also be readily scaled up to industrial operation.

SUMMARY OF INVENTION

The present inventors have found that oxidation or racemisation of the double bonds is a serious problem for the molecules described herein. The chemistry described herein avoids or at least reduces the formation of racemised products and enables the formation of a polyunsaturated thiol which can be used in further (known) synthetic steps to form desired target molecules. More specifically, we have found a method of making a polyunsaturated thiol compound, which can ultimately be converted to the advantageous ketone compounds discussed herein, in which unwanted oxidation and cis/trans isomerization reactions are substantially reduced or eliminated. Practice of the invention methods can be used to produce a variety of polyunsaturated ketone compounds suitable for pharmaceutical use including those specified herein.

It is therefore an object of the invention to prepare pharmaceutically-acceptable polyunsaturated thiol compounds, which can ultimately be converted to the advantageous ketone compounds discussed herein, in which unwanted oxidation and cis/trans isomerization reactions are substantially reduced or eliminated. The method of the invention involves conversion of a polyunsaturated alcohol to a sulphonyl ester (i.e. a compound comprising the group —$OSO_2$—Rx where Rx is a $C_{1-20}$ hydrocarbyl group), conversion of that sulphonyl ester to a thioester (of formula —SCORy wherein Ry is a $C_{1-20}$ hydrocarbyl group) and then reduction of that thioester to a thiol (—SH) in the presence of an anti-oxidant.

It is also an object of the invention to provide the target compounds in high purity, such as that which is often required by regulatory authorities.

Preferably, subsequent steps towards the formation of the polyunsaturated ketone are also performed in the presence of a pharmaceutically acceptable anti-oxidant so as to minimize potential for oxidation or cis/trans isomerization in subsequent reactions.

It is also within the scope of the invention if the polyunsaturated alcohol used is prepared via contact of a polyunsaturated aldehyde with a suitable electrophilic reducing agent under conditions sufficient to make the polyunsaturated alcohol. It is again believed that use of mild electrophilic reducing agents reduces unwanted reduction of double bonds, thereby helping the overall synthesis achieve better purity.

Thus, viewed from one aspect the invention provides a process for the preparation of a polyunsaturated thiol comprising:

(1) reacting a polyunsaturated alcohol in the presence of a compound of formula $R_2$—$SO_2$Hal wherein $R_2$ is a $C_{1-20}$ hydrocarbyl group, such an $C_{1-10}$ alkyl group, to form a polyunsaturated sulphonyl ester;

(2) converting the polyunsaturated sulphonyl ester to a polyunsaturated thioester by reacting with an anion of formula $^-SC(=O)R_4$ wherein $R_4$ is a $C_{1-20}$ hydrocarbyl group;

(3) converting the polyunsaturated thioester into a polyunsaturated thiol optionally in the presence of an antioxidant.

Viewed from another aspect the invention provides a process for the preparation of an polyunsaturated ketone compound comprising:

steps (1) to (3) above and subsequently, (4) reacting said polyunsaturated thiol with a compound (LG)$R^3$COX wherein X is an electron withdrawing group and $R^3$ is an alkylene group carrying a leaving group (LG), such as LG-$CH_2$— forming

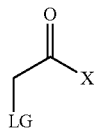

i.e. where $R^3$ is —$CH_2$— where X is an electron withdrawing group and LG is a leaving group; optionally in the presence of an antioxidant, so as to form a polyunsaturated ketone compound, ideally of formula (VIII) as herein defined.

Viewed from another aspect the invention provides the product of a process as hereinbefore defined.

Viewed from another aspect the invention provides a process for the preparation of a polyunsaturated thiol of formula (VII) or (VII')

R—SH or R'—SH    (VII) or (VII')

comprising:
(1) reacting a polyunsaturated alcohol of formula

R—OH or R'—OH    (I) or (I')

wherein R is an optionally substituted $C_{9-23}$ unsaturated hydrocarbon group optionally interrupted by one or more heteroatoms or groups of heteroatoms selected from S, O, N, SO, $SO_2$, said hydrocarbon group comprising at least 2, preferably at least 4 double bonds; and wherein R' is a linear, unsubstituted $C_{9-23}$ unsaturated hydrocarbon group, said hydrocarbon group comprising at least 2, preferably at least 4 double bonds;

in the presence of a compound of formula $R_2$—$SO_2$Hal wherein $R_2$ is a $C_{1-20}$ hydrocarbyl group, such an $C_{1-10}$ alkyl group, to form a polyunsaturated sulphonyl ester compound of formula (V) or (V')

R—$OSO_2R_2$ or R'$OSO_2R_2$    (V) or (V')

(2) converting the polyunsaturated sulphonyl ester (V) or (V') to a polyunsaturated thioester by reacting with an anion of formula $^-SC(=O)R_4$ wherein $R_4$ is a $C_{1-20}$ hydrocarbyl group to form a polyunsaturated thioester compound of formula (VI) or (VI'):

R—$SCOR_4$ or R'—$SCOR_4$    (VI) or (VI')

wherein R and R' are as hereinbefore defined;

(3) converting the polyunsaturated thioester optionally in the presence of an antioxidant and optionally in the presence of a metal carbonate to form a polyunsaturated thiol compound of formula (VII) or (VII')

R—SH or R'—SH    (VII) or (VII').

wherein R and R' are as hereinbefore defined.

Viewed from another aspect the invention provides a process including at least the following steps:

(1) reacting (3Z,6Z,9Z,12Z,15Z)-octadeca-3,6,9,12,15-pentaen-1-ol

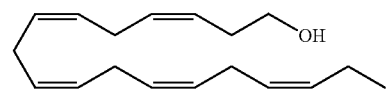

or (2E,6Z,9Z,12Z,15Z)-octadeca-2,6,9,12,15-pentaen-1-ol;

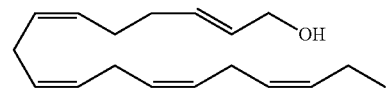 [SMILES: CC/C=C\C/C=C\C/C=C\C/C=C\CC/C=C/CO]

with methanesulphonyl chloride in the presence of a base so as to form a

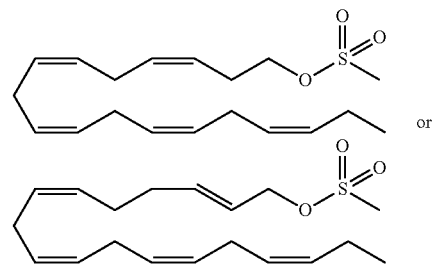

(2) reacting the reaction product of step (1) with a thioacetate ion to form a thioester of formula:

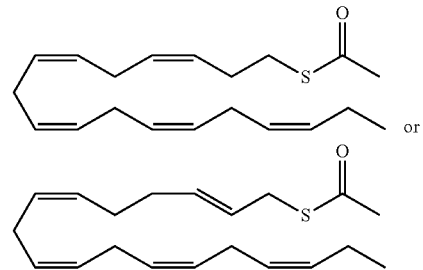

(3) reacting the product of step (2) with potassium carbonate in the presence of an antioxidant to form a thiol of formula:

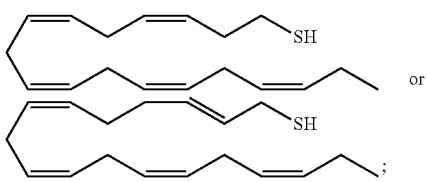

(4) optionally contacting the thiol produced in step (3) with 3-bromo-1,1,1-trifluoroacetone under conditions that produce

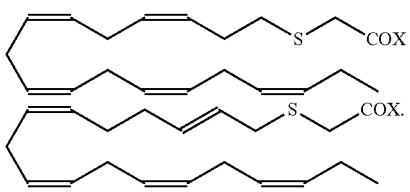

where X is $CF_3$.

In any process of the invention, it is further preferred if the polyunsaturated alcohol is obtained by reduction of its corresponding aldehyde in the presence of an electrophilic reducing agent such as DIBAH (diisobutylaluminium hydride).

Viewed from another aspect the invention provides a pharmaceutical composition comprising the product of a process as hereinbefore defined and at least one pharmaceutically acceptable excipient.

Definitions

The term polyunsaturated in the term polyunsaturated thiol or polyunsaturated thioester and so on refers to compounds which contains a hydrocarbon chain containing multiple double bonds, i.e. 2 or more. That chain is preferably free of any rings. It is preferred if double bonds present are not conjugated.

The term Hal means halide, i.e. F, Cl, Br or I, preferably Cl or Br.

The term $C_{1-20}$ hydrocarbyl group refers to a group containing 1 to 20 carbon atoms and H atoms only. The group may be a $C_{1-10}$ hydrocarbyl group, such as a $C_{1-10}$ alkyl group, $C_{2-10}$ alkenyl, $C_{6-10}$ aryl group, $C_{7-10}$ alkylaryl, $C_{7-10}$ arylalkyl group, $C_{3-10}$-cycloalkyl group, $C_{4-10}$ alkylcycloalkyl or $C_{4-10}$ cycloalkylalkyl group and so on. As long as there are only C and H atoms present and up to 20 carbon atoms, any arrangement of those atoms is possible. Any hydrocarbyl group is preferably a $C_{1-10}$ alkyl group. Any hydrocarbyl group is preferably a linear $C_{1-10}$ alkyl group.

Generally, any polyunsaturated compound of the invention will have an Mw of less than 500 g/mol, preferably 450 g/mol or less, more preferably 400 g/mol or less.

The term "pharmaceutically acceptable" means that which is useful in preparing a pharmaceutical that is generally non-toxic and is not biologically undesirable and includes that which is acceptable for veterinary use and/or human pharmaceutical use.

DETAILED DESCRIPTION OF INVENTION

This invention relates to a process for the manufacture of a polyunsaturated thiol and ultimately a polyunsaturated ketone. The process offers high yields and high purity. In particular, it is envisaged that after suitable purification the process steps of the invention provide the target compounds in pharmaceutical grade. The process can also be readily scaled up for industrial operation.

The invention provides a way of making a polyunsaturated thiol and subsequent conversion of that thiol to a ketone under conditions that provide the compounds in yields and purities that are often required by regulatory authorities. For example, and without wishing to be bound by theory, it is believed that production of unwanted oxidation products and unwanted double bond racemisation, can be decreased or even eliminated following the techniques described herein.

The starting material in the process of the invention is a polyunsaturated alcohol. Preferably that polyunsaturated alcohol is of formula (I)

$$R\text{—}OH \tag{I}$$

wherein R is an optionally substituted $C_{9-23}$ unsaturated hydrocarbon group optionally interrupted by one or more heteroatoms or groups of heteroatoms selected from S, O, N, SO, $SO_2$, said hydrocarbon group comprising at least 2, preferably at least 4 double bonds.

It is preferred if in any group R, double bonds are not conjugated. The group R preferably comprises 5 to 9 double bonds, preferably 5 or 8 double bonds, e.g. 5 to 7 double bonds such as 5 or 6 double bonds.

It is also preferred if the double bonds do not conjugate with the hydroxyl group.

The double bonds present in the group R may be in the cis or trans configuration however, it is preferred if the majority of the double bonds present (i.e. at least 50%) are in the cis configuration. In further advantageous embodiments all the double bonds in the group R are in the cis configuration or all double bonds are in the cis configuration except the double bond nearest the OH group which may be in the trans configuration.

The group R may have between 9 and 23 carbon atoms, preferably 11 to 19 carbon atoms, especially 16 to 18 carbon atoms. Carbon atoms are preferably linear in the R group.

Whilst the R group can be interrupted by at least one heteroatom or group of heteroatoms, this is not preferred and the R group backbone preferably contains only carbon atoms.

The R group may by optionally substituted, e.g. carry up to three substituents, e.g. selected from halo, $C_{1-6}$ alkyl e.g. methyl, $C_{1-6}$ alkoxy. If present the substituents are preferably non-polar, and small, e.g. a methyl group. It is preferred however, if the R group remains unsubstituted.

The R group is preferably linear, i.e. there are no branches in the R chain. It preferably derives from a natural source such as a long chain fatty acid or ester. In particular, the R group may derive from arachidonic acid, docosahexaenoic acid or eicosapentaenoic acid.

It is thus preferred if the polyunsaturated alcohol is a compound of formula (I')

$$R'\text{—}OH \tag{I}$$

wherein R' is a linear, unsubstituted $C_{9-23}$ unsaturated hydrocarbon group, said hydrocarbon group comprising at least 2, preferably at least 4 double bonds. Ideally, R' is an alkenylene group having 9-23 carbon atoms and at least 2, such as at least 4 double bonds. Preferred options for R also apply to the definition of R'.

It may be that the polyunsaturated alcohol of use in the invention derives from a corresponding fatty acid or aldehyde. We have further found that when the polyunsaturated alcohol derives from its corresponding aldehyde, that polyunsaturated alcohol is preferably obtained in a reaction that involves contacting a polyunsaturated aldehyde with a suitable electrophilic reducing agent under conditions sufficient to make the polyunsaturated alcohol. Without wishing to be bound to any theory, it is believed that use of mild electrophilic reducing agents reduce unwanted reduction of double bonds, thereby helping the overall synthesis achieve better yields and purity. The polyunsaturated aldehyde is therefore preferably of formula R—CHO or R'—CHO where R and R' are as hereinbefore defined.

The use of diisobutylaluminium hydride (DIBAH) is particularly preferred in this regard. The present inventors have surprisingly found that some other well known reducing agents such as sodium borohydride cannot be used successfully in this reduction as they increase the number of impurities formed. It is surprising that the use of DIBAH seems to reduce isomerism and hence minimises impurity formation.

The invention further comprises therefore conversion of a compound of formula (II) or (II')

$R_1CHO$ or $R_{1'}CHO$            (II) or (II')

to R—OH or R'—OH using DIBAH where R and R' are as hereinbefore defined and $R_1$ and $R_{1'}$ are equivalent to R and R' from which a terminal —$CH_2$— link is removed. It will be appreciated that the definition of $R_1$ and $R_{1'}$, depend on the definition of R and R'. During the reduction of the aldehyde a —$CH_2$— group is generated from which forms part of the R or R' definition and hence the $R_1$ and $R_{1'}$, chains are one carbon shorter than those or R and R'. Alternatively viewed, the reaction involves the reduction:

$R_1CHO$ or $R_{1'}CHO$ (II) or (II')→$R_1CH_2$—OH or to $R_{1'}CH_2$—OH            (III) or (III')

wherein $R^1$ is an optionally substituted $C_{8-22}$ unsaturated hydrocarbon group optionally interrupted by one or more heteroatoms or groups of heteroatoms selected from S, O, N, SO, $SO_2$, said hydrocarbon group comprising at least 2, preferably at least 4 double bonds; and wherein $R_1$' is a linear, unsubstituted $C_{8-22}$ unsaturated hydrocarbon group, said hydrocarbon group comprising at least 2, preferably at least 4 double bonds. Preferred options for R also apply to the definition of $R_1$ and $R_{1'}$. (subtracting one carbon atom from any carbon limits).

The aldehyde can be prepared by any suitable technique such as those described in J Chem Soc Perkin Trans 1, 2000, 2271-6. Alternatively, a protocol as outlined in Molecules 2014 (19), 3804-3811 may be followed. A suitable process would be:

In another embodiment as explained in J Chem Soc Perkin Trans 1, 2000, 2271-6, the alcohol can be prepared via a reduction of a fatty acid ester, conversion to an epoxide, reduction thereof to an aldehyde, optional isomerisation and further reduction. The scheme below summarises the reactions for AVX001:

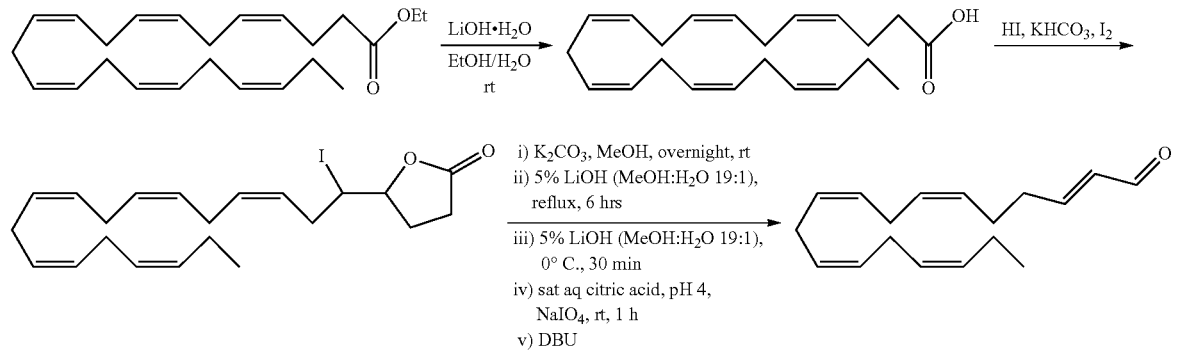

The alcohol for the production of AVX002 can be prepared directly from a reduction of the aldehyde without an isomersation.

It is preferred if the alcohol starting material used in the process of the invention is purified using normal phase column chromatography or, preferably, reversed phase column chromatography.

In one embodiment therefore, the alcohol starting material for the process of the invention is obtained via the following reactions:

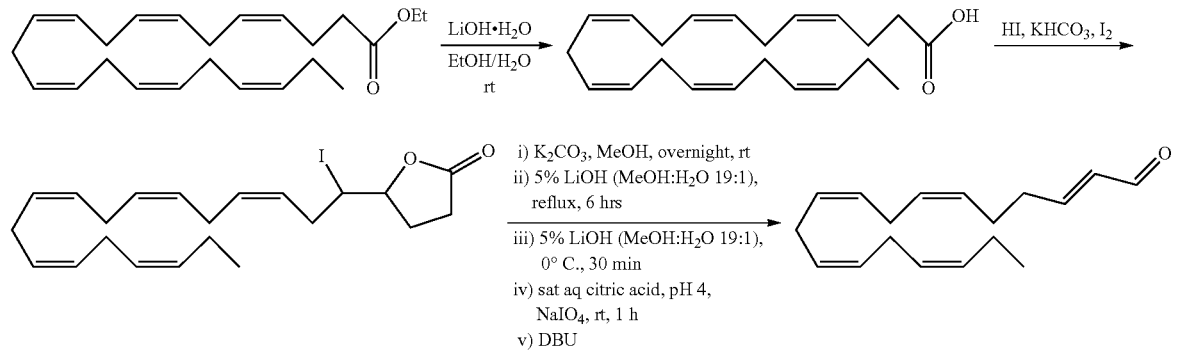

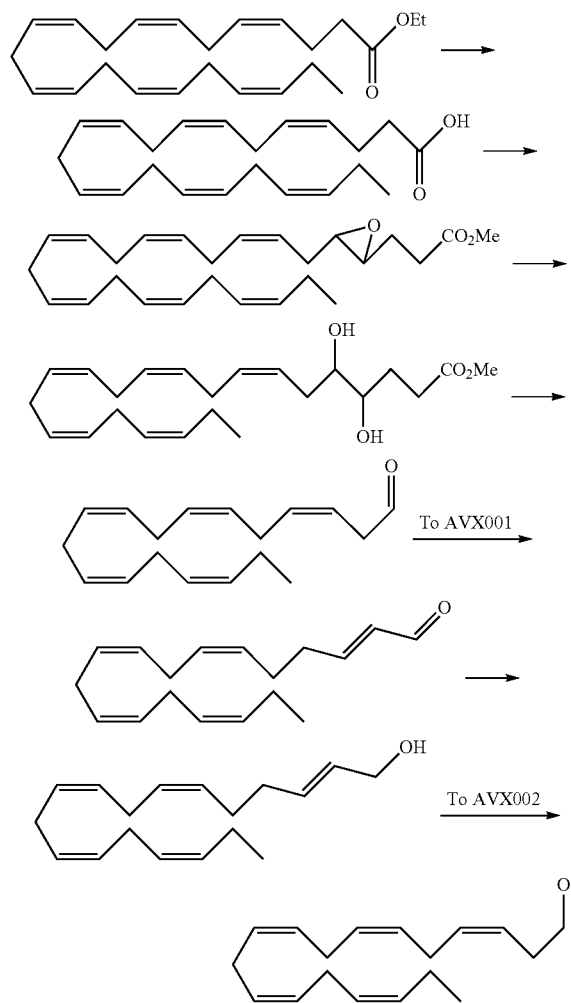

The polyunsaturated alcohol is reacted with a sulphonyl halide, i.e. a compound of formula:

R$_2$SO$_2$Hal    (IV)

where R$_2$ is a C$_{1-20}$ hydrocarbyl group, preferably C$_{1-10}$ hydrocarbyl group, especially C$_{1-10}$ alkyl group, such as C$_{1-4}$ alkyl group, especially methyl. R$_2$ is preferably a linear C$_{1-20}$ hydrocarbyl group such as linear C$_{1-10}$ alkyl group.

The halide (hal) can be F, Cl, Br or I, especially Br or Cl, most especially Cl.

The reaction of the polyunsaturated alcohol with the sulphonyl halide is preferably effected in the presence of a base, ideally to neutralise any halide acids (e.g. HCl) that form during the reaction. The base should not itself react with the polyunsaturated compounds. Suitable bases are well known in the art, such as trialkylamines, in particular triethylamine. Well known non nucleophilic bases are therefore appropriate.

This reaction preferably forms therefore a compound of formula (V) or (V'):

R—OSO$_2$R$_2$ or R'OSO$_2$R$_2$    (V) or (V')

wherein R, R' and R$_2$ are as hereinbefore defined.

For the avoidance of doubt, R—OSO$_2$R$_2$ has the structure:

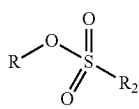

Step (2) of the process of the invention requires the conversion of the sulphonyl ester (V)/(V') into a thioester. The —OSO$_2$R$_2$ group is thus converted into —SC(=O)R$_4$ group.

This can be achieved by reaction using a compound comprising a salt with a SCOR$_4$ ion where R$_4$ is a C$_{1-20}$ hydrocarbyl group. The counterion can be a metal such as an alkali metal, e.g. Li, Na or K. R$_4$ is preferably a C$_{1-10}$ hydrocarbyl group, especially a C$_{1-10}$ alkyl group, such as C$_{1-6}$ alkyl group especially C$_{1-4}$ alkyl group such as methyl. Any R$_4$ group is preferably linear. The use of thioacetate ions is thus preferred.

The reaction forms a compound (VI) or (VI')

R—SCOR$_4$ or R'—SCOR$_4$    (VI) or (VI')

wherein R, R' and R$_4$ are as hereinbefore defined.

In step (3) of the process, this thioester is then converted to a thiol. Whilst this can in theory be carried out using any conventional process, e.g. using diisobutylaluminium hydride, in order to avoid side reaction, impurity formation and cis-trans isomerisation of double bonds present, the inventors propose carrying out this reaction in the presence of an anti-oxidant.

It is preferred if the anti-oxidant is a small molecule such as one having a molecular weight of 500 g/mol or less, such as 250 g/mol or less. The anti-oxidant should ideally be approved for use by the FDA.

The anti-oxidant used is preferably butyl hydroxyanisole, butyl hydroxytoluene, propyl gallate, tocopherol, ascorbic acid, ascorbyl palmitate, thioglycerol, thioglycolic acid, sodium bisulphite, sodium sulphite, sodium metabisulphite, edetate tetrasodium, or EDTA.

The use of tocopherol is especially preferred, particularly (+/−)-alpha-tocopherol.

The amount of anti-oxidant added/present may be of the order of 0.01 to 1 mol %, preferably 0.1 to 0.5 mol % relative to the amount of polyunsaturated thioester present (in mols).

Also, the foregoing beneficial effects can be further enhanced by making the polyunsaturated thiol in a reaction that involves contacting a polyunsaturated thioester with a suitable mild electrophilic reducing agent under conditions sufficient to make the polyunsaturated thiol. Without wishing to be bound to any theory, it is believed that use of mild electrophilic reducing agents, as discussed below, reduce unwanted reduction of double bonds, thereby helping the overall synthesis achieve better yields and purity.

Suitable reducing agents are ideally metal carbonates such as alkali metal carbonates, especially potassium carbonate. The use of a solvent such as methanol is appropriate. The use therefore of a metal carbonate along with an antioxidant is especially preferred.

Preferred thiols that are formed are simply of formula (VII) or (VII')

R—SH or R'—SH    (VII) or (VII')

wherein R and R' are as hereinbefore defined.

Ideally, the thiol should have a purity of at least 90% as determined by HPLC (% area) at this point. More preferably purity should be 91% or more, such as 92% or more, ideally 93% or more, especially 94% or even 95% or more.

The process herein has been found to produce the thiol in high yield, e.g. 70% or more from step (1), such as 75% or more, even 80% or more. Also, we can eliminate the presence of impurities detectable on HPLC.

Ideally of course, the process of the invention targets a variety of pharmaceutically-acceptable polyunsaturated ketones that are suitable for pharmaceutical use. Preferred compounds include a ketone group comprising an electron withdrawing group and a sulphur atom in the α, β, γ, or δ position from the ketone group. An electron withdrawing group or EWG draws electrons away from a reaction centre.

Preferred polyunsaturated ketone targets of the invention are therefore of formula (VIII)

$$R^5\text{—CO—X} \qquad (VIII)$$

wherein $R^5$ is a $C_{10-24}$ polyunsaturated hydrocarbon group interrupted α, β, γ, or δ position from the ketone group by a S atom; and X is an electron withdrawing group (EWG).

Suitable electron withdrawing groups X for any compound of the invention are CN, phenyl, $CHal_3$, $CHal_2H$, $CHalH_2$ wherein Hal represents a halogen, especially F. The EWG is especially $CHal_3$, e.g. $CF_3$.

It is most preferred if the S atom is beta to the carbonyl (thus forming a group R—S—$CH_2COCF_3$ where R is as hereinbefore defined).

It is preferred if in any group $R^5$, double bonds are not conjugated. The group $R^5$ preferably comprises 5 to 9 double bonds, preferably 5 or 8 double bonds, e.g. 5 to 7 double bonds such as 5 or 6 double bonds.

It is also preferred if the double bonds do not conjugate with the carboxyl group.

The double bonds present in the group $R^5$ may be in the cis or trans configuration however, it is preferred if the majority of the double bonds present (i.e. at least 50%) are in the cis configuration. In further advantageous embodiments all the double bonds in the group $R^5$ are in the cis configuration or all double bonds are in the cis configuration except the double bond nearest the S group which may be in the trans configuration.

The group $R^5$ may have between 10 and 24 carbon atoms, preferably 12 to 20 carbon atoms, especially 17 to 19 carbon atoms. The group $R^5$ is thus preferably an alkenylene group having between 10 and 24 carbon atoms, preferably 12 to 20 carbon atoms, especially 17 to 19 carbon atoms and at least two double bonds. The $R^5$ group is preferably linear.

Ideally therefore the target compounds of the invention are of formula R—$SCH_2COCF_3$ or R'$SCH_2COCF_3$ where R and R' are as hereinbefore defined.

In a preferred embodiment, the invention provides a method of producing a pharmaceutically acceptable 1,1,1-trifluoro-3-(((2E,6Z,9Z,12Z,15Z)-octadeca-2,6,9,12,15-pentaein-1-yl)thio)propan-2-one:

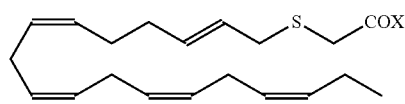

where X is $CF_3$; or related compound

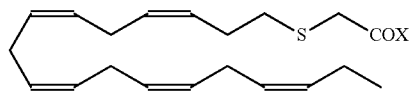

where X is $CF_3$.

The last step of the process of the invention therefore involves reaction of the thiol with a suitable ketone to form the desired compounds of formula (VIII). The reaction preferably involves a compound is of formula (LG)$R^3$CO—X where $R^3$ reflects the atoms necessary to complete the $R^5$ group where $R^5$=R—S—$R^3$—; i.e.

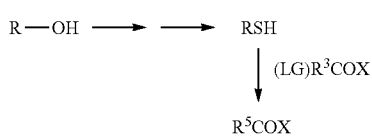

$R^3$ is preferably $C_{1-3}$-alkylene, such as methylene. LG represents a leaving group which is nucleophilicly substituted by the thiol group. A leaving group is a molecular fragment that departs with a pair of electrons in heterolytic bond cleavage. Preferably of course, (LG)$R^3$—COX represents the compound LG-$CH_2$—COX, where LG is a leaving group such as a halide, tosyl, mesyl and so on. Ideally LG is a halide such as Br. X is an electron withdrawing group as hereinbefore defined in the above formulae, preferably $CF_3$ again. Most preferably (LG)$R^3$—COX is $BrCH_2$—$COCF_3$.

This final reaction step may take place in the presence of anti-oxidant as hereinbefore defined. An anti-oxidant might inherently be present as carry over from the thioester conversion step and in that scenario, it may not be necessary to add more anti-oxidant. It is within the scope of the invention however, to add more anti-oxidant, e.g. where the thiol formed was purified and hence anti-oxidants removed.

It is preferred if the anti-oxidant is a small molecule such as one having a molecular weight of 500 g/mol or less, such as 250 g/mol or less. The anti-oxidant should ideally be approved for use by the FDA.

The anti-oxidant used is preferably butyl hydroxyanisole, butyl hydroxytoluene, propyl gallate, tocopherol, ascorbic acid, ascorbyl palmitate, thioglycerol, thioglycolic acid, sodium bisulphite, sodium sulphite, sodium metabisulphite, edetate tetrasodium, or EDTA.

The use of tocopherol is especially preferred, particularly (+/−)-alpha-tocopherol.

The reaction from thiol to ketone may also be encouraged by use of a mild base such as a hydrogen carbonate salt to encourage nucleophilic attack of the thiol on the leaving group of the ketone reactant.

It will be appreciated that the reaction products of every step of the process of the invention can be purified using well known procedures.

It will be appreciated that the compounds of the invention are primarily for medicinal use and hence any anti-oxidant employed is preferably pharmaceutically acceptable.

The amount of antioxidant added to the polyunsaturated thiol may be between 0.01 to 1 mol %, 0.1 to 0.5 mol % of the polyunsaturated thiol.

They have also learned that the presence of a pharmaceutically-acceptable anti-oxidant can be used in the present methods to help reduce unwanted cis/trans isomerization without being destroyed or otherwise blocked.

It will be appreciated that any reaction described herein may need to be carried out in the absence of oxygen, e.g. under an Ar atmosphere.

Ideally, the ketone formed by the process of the invention should have a purity of at least 90% as determined by HPLC (% area) at this point. More preferably purity should be 91% or more, such as 92% or more, ideally 93% or more, especially 94% or even 95% or more.

The process herein has been found to produce the ketone in high yield, e.g. 70% or more from step (1). Also, we can eliminate the presence of impurities detectable on HPLC.

In a most preferred embodiment, the process of the invention includes at least the following steps:

(1) reacting (3Z,6Z,9Z,12Z,15Z)-octadeca-3,6,9,12,15-pentaen-1-ol

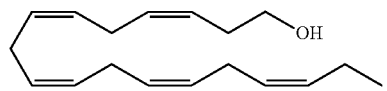

or (2E,6Z,9Z,12Z,15Z)-octadeca-2,6,9,12,15-pentaen-1-ol;

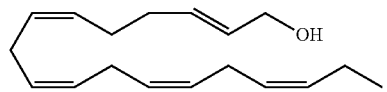 [SMILES: CC/C=C\C/C=C\C/C=C\C/C=C\CC/C=C/CO]

with methanesulphonyl chloride in the presence of a base so as to form a

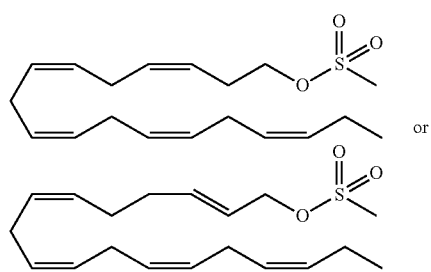

(2) Reacting the reaction product of step (1) with a thioacetate ion to form a thioester of formula:

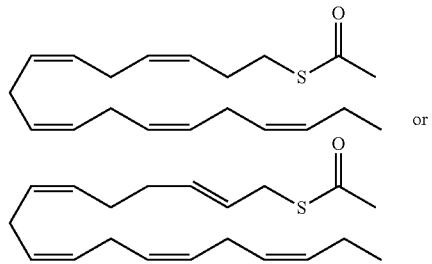

(3) Reacting the product of step (2) with potassium carbonate in the presence of an antioxidant to form a thiol of formula:

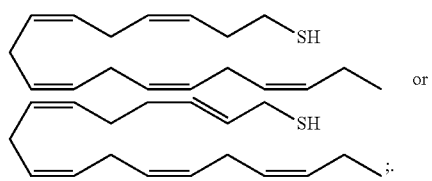

(4) optionally contacting the thiol produced in step (3) with 3-bromo-1,1,1-trifluoroacetone under conditions that produce

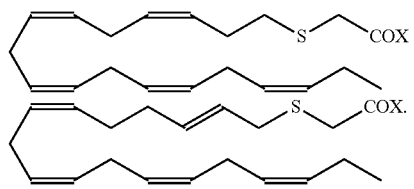

where X is $CF_3$.

In particular, the invention relates to the process summarised in scheme 1:

Scheme 1

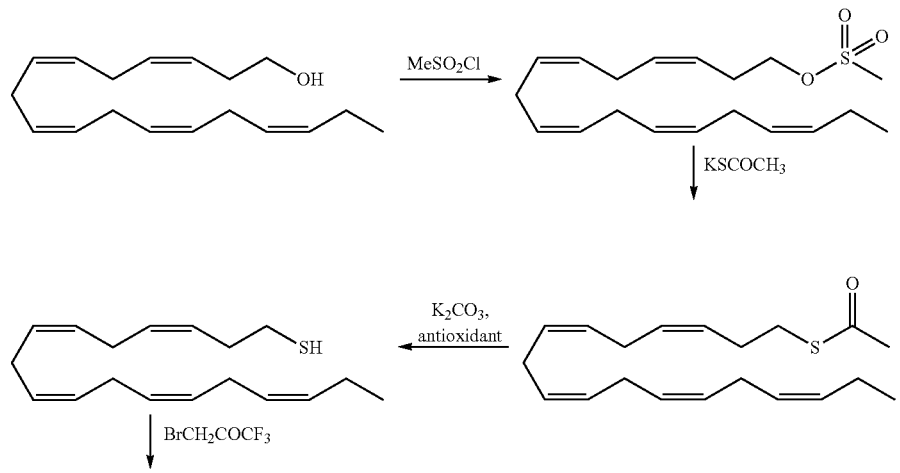

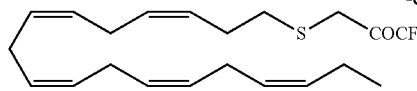

That compound can be purified in by dry-column vacuum chromatography (Synthesis, 2001; 16:2431-2434) to at least 90% purity as determined by HPLC (% area) to produce a pharmaceutically acceptable compound.

The invention also relates, in particular, to the process summarised in method 1:

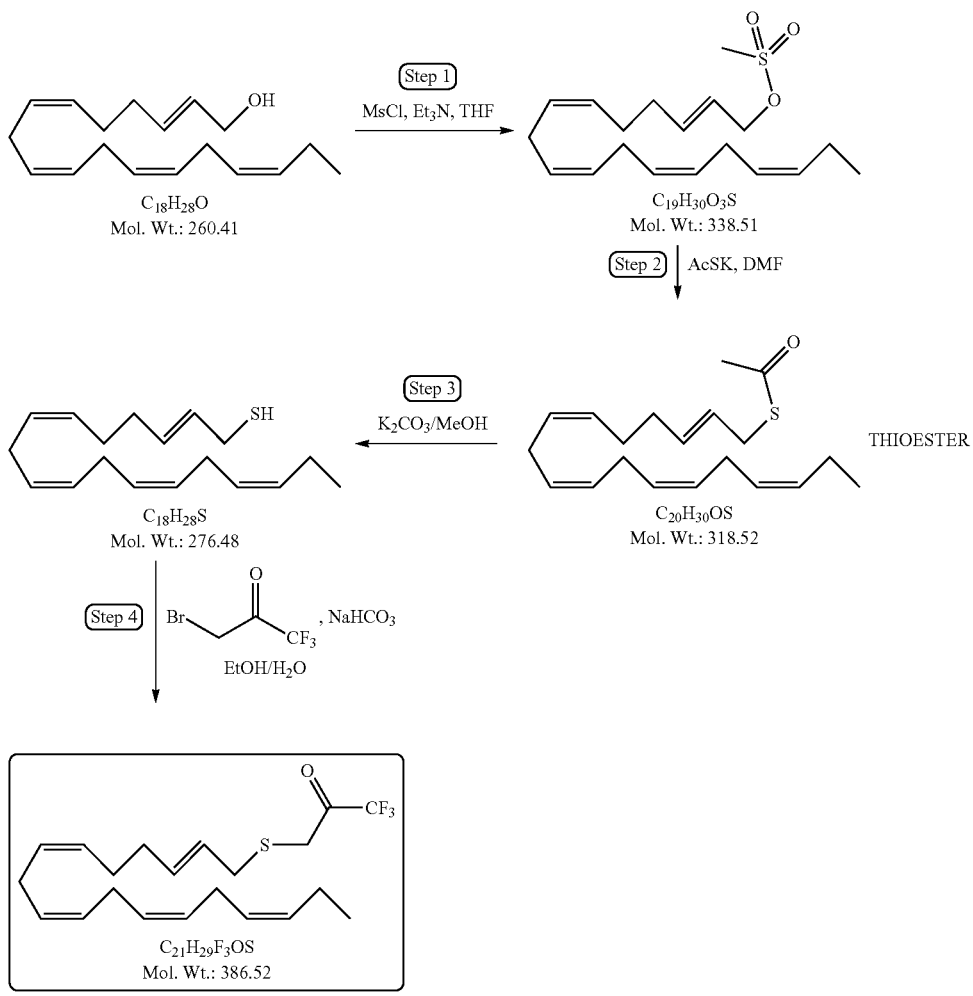

METHOD 1

Compound of the invention can also be purified, e.g. by normal phase or reverse phase column chromatography to produce a pharmaceutically acceptable compound.

It will be appreciated that the compounds made in the process of the invention have a variety of applications, e.g. in the treatment of chronic inflammatory disorders. They can be formulated as pharmaceutical compositions using well known techniques. They may be converted into salts where appropriate. A further discussion of such techniques is not required here.

The invention will now be described with reference to the following non limiting examples.

Example 1

Preparation of AVX002

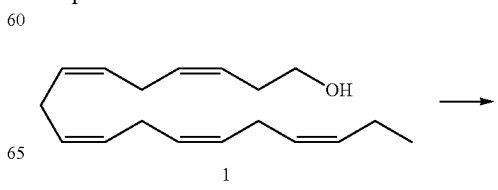

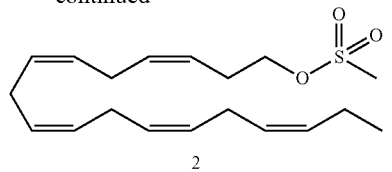

2

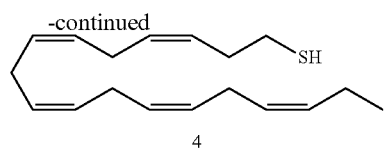

4

To a solution of 1 (5.12 g, 19.7 mmol) in dry tetrahydrofuran (50 mL) at 0° C. was added methanesulfonyl chloride (1.7 mL, 22.0 mmol) with stirring, followed by triethylamine (5.5 mL, 39.4 mmol). A precipitation formed immediately, giving a slurry. The cooling bath was removed and the reaction mixture stirred for one hour. The reaction mixture was poured into water (200 mL), 40 mL 1 M HCl added and the aqueous phase extracted with diethyl ether (3×50 mL). The combined organic phase was washed with 5% NaHCO$_3$ (aq., 50 mL) and brine (50 mL), and subsequently dried over Na$_2$SO$_4$. Filtration and evaporation of solvent under reduced pressure yielded 6.40 g (95.9% yield) of 2 as a yellow-orange oil, which was used in the next step without purification. $^1$H NMR (CDCl$_3$, 300 MHz): d 0.97 (3H, t, J=7.5 Hz), 2.07 (2H, dq, J$_1$=J$_2$=7.3 Hz), 2.54 (2H, dt, J$_1$=J$_2$=6.9 Hz), 2.78-2.88 (8H, m), 3.00 (3H, s), 4.22 (2H, t, J=6.9 Hz), 5.25-5.46 (9H, m), 5.51-5.62 (1H, m). MS (ES): m/z 361 (M+Na)$^+$.

Compound 3 (5.60 g, 17.6 mmol) was dissolved in methanol (50 mL) containing 10 mg α-tocopherol. Potassium carbonate (2.68 g, 19.4 mmol) was added in one portion at room temperature and the mixture stirred for 45 minutes under inert atmosphere. The reaction mixture was quenched by way of drop-wise addition of 50 mL 1 M HCl, while cooling the mixture on an ice-bath. The mixture was subsequently extracted with heptane (3×50 mL), and the combined organic phases was washed with brine (50 mL) and dried over Na$_2$SO$_4$. After filtration and removal of solvent under reduced pressure, 4.77 g of 4 (98.0% yield) was obtained as a pale yellow oil.

Spectral data, compound 4

$^1$H NMR (CDCl$_3$, 400 MHz): ☐ 0.98 (3H, t, J=7.5 Hz), 1.43 (1H, t, J=7.7 Hz), 2.08 (2H, dq, J$_1$=J$_2$=7.5 Hz), 2.40 (2H, dt, J$_1$=J$_2$=7.0 Hz), 2.57 (2H, dt, J$_1$=J$_2$=7.3 Hz), 2.79-2.89 (8H, m), 5.29-5.43 (9H, m), 5.46-5.53 (1H, m).

The crude product was used in the next step without further purification.

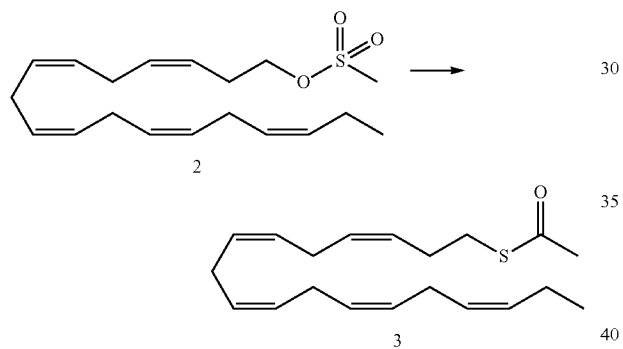

To a solution of 2 (6.40 g, 18.9 mmol) in dry DMF (65 mL) was added potassium thioacetate (8.48 g, 74.2 mmol) in one portion, accompanied by a slight colour change towards brown and an increase in viscosity. The reaction mixture was stirred under inert atmosphere for 1.5 hours at room temperature, and poured into water (500 mL). The product was extracted with ether (3×100 mL), and combined organic phases washed with brine (2×100 mL) and dried over Na$_2$SO$_4$. After filtration, the solvent was removed under reduced pressure, giving 5.76 g crude product. Subsequent purification using dry column vacuum chromatography (DCVC, gradient elution n-heptane—100:1 n-heptane:ethyl acetate) gave 5.60 g of 3 (93.0% yield) as a pale yellow oil. $^1$H NMR (CDCl$_3$, 400 MHz): d 0.97 (3H, t, J=7.5 Hz), 2.08 (2H, dq, J$_1$=J$_2$=7.1 Hz), 2.32 (3H, s), 2.35 (2H, dt, J$_1$=J$_2$=7.0 Hz), 2.79-2.87 (8H, m), 2.90 (2H, t, J=7.3 Hz), 5.27-5.49 (10H, m). MS (ES): m/z 341 (M+Na)$^+$.

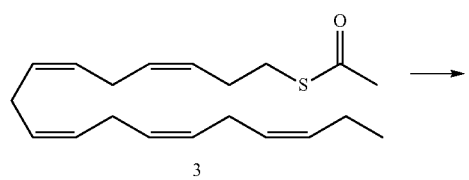

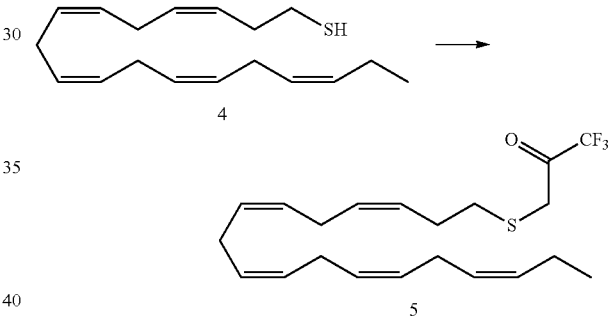

Sodium hydrogen carbonate (1.97 g, 23.4 mmol) was added to thiol 4 (3.07 g, 11.1 mmol), followed by water (40 mL) and ethanol (60 mL). The resulting inhomogeneous mixture was stirred vigorously at room temperature for 20 min under inert atmosphere. 3-Bromo-1,1,1-trifluoroacetone (1.40 ml, 13.3 mmol) was then added in one portion, and stirring was continued for 45 minutes. The reaction mixture was extracted with n-heptane (2×50 ml). The combined organic phase was washed with brine (50 mL), dried over Na$_2$SO$_4$, filtered and concentrated under reduced pressure. The crude product was purified using dry column vacuum chromatography (DCVC, gradient elution n-heptane—100:10 n-heptane:ethyl acetate). Pure fractions were combined, and subsequent evaporation of solvent under reduced pressure gave 3.43 g of 5 (79.9% yield) as a colourless oil.

Spectral data, compound 5:

$^1$H NMR (mixture of hydrated/unhydrated), CDCl$_3$, 400 MHz): ☐ 0.98 (3H, t, J=7.5 Hz), 2.08 (2H, dq, J$_1$=J$_2$=7.2 Hz), 2.39 (2H, m), 2.57 (1H, t, J=7.3 Hz), 2.77 (1H, t, J=7.5 Hz), 2.80-2.88 (8H, m), 2.92 (1H, s), 3.51 (1H, s), 3.98 (1H, s), 5.29-5.51 (10H, m). $^{13}$C NMR (mixture of hydrated/unhydrated, CDCl$_3$, 100 MHz): ☐ 14.2, 20.5, 25.5, 25.58, 25.60, 25.67, 25.70, 26.5, 27.1, 31.7, 33.3, 34.7, 36.4, 92.4 (q, J$_{C-F}$=31 Hz), 115.5 (q, J$_{C-F}$=293 Hz), 122.9 (q, J$_{C-F}$=286 Hz), 126.8, 127.0, 127.1, 127.7, 127.77, 127.79, 127.9, 128.0, 128.3, 128.40, 128.43, 128.55, 128.57, 130.1, 130.2, 131.99, 132.01, 185.0 (q, $J_{C-F}$=34 Hz). MS (ES): m/z 385 (M-H$^+$)$^-$.

Example 2

Preparation of AVX001

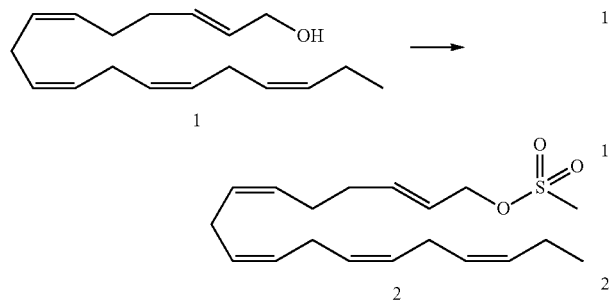

To a solution of 1 (5.03 g, 19.3 mmol) in dry tetrahydrofuran (50 mL) at 0° C. was added methanesulfonyl chloride (1.7 mL, 22.0 mmol) with stirring, followed by triethylamine (5.5 mL, 39.4 mmol). A precipitation formed immediately, giving a slurry. The cooling bath was removed and the reaction mixture stirred for one hour. The reaction mixture was poured into water (200 mL), 40 mL 1 M HCl added and the aqueous phase extracted with diethyl ether (3×50 mL). The combined organic phase was washed with 5% NaHCO$_3$ (aq., 50 mL) and brine (50 mL), and subsequently dried over Na$_2$SO$_4$. Filtration and evaporation of solvent gave quantitative yield of crude 2, which was used directly in the next step without purification.

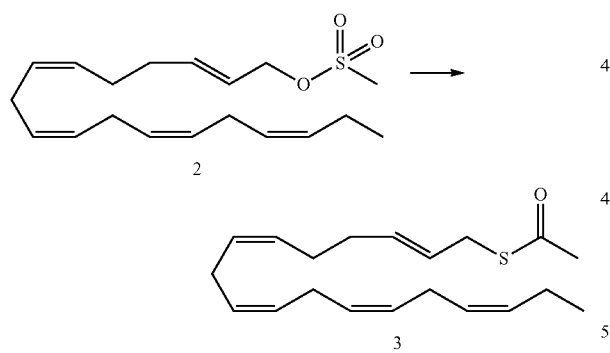

The crude product of 2 was dissolved in dry DMF (65 mL), to which potassium thioacetate (8.83 g, 77.3 mmol) in one portion, accompanied by a change of colour to brown and a large increase in viscosity. The reaction mixture was stirred under inert atmosphere overnight at room temperature, and quenched with water (500 mL). The product was extracted with ether (3×100 mL), and combined organic phases washed with brine (2×100 mL) and dried over Na$_2$SO$_4$. After filtration, the solvent was removed under reduced pressure, giving 5.44 g crude product. Subsequent purification using dry column vacuum chromatography (DCVC, gradient elution n-heptane—100:1 n-heptane:ethyl acetate) gave 5.27 g of 3 (85.5% yield over two steps) as an orange oil. $^1$H NMR (CDCl$_3$, 400 MHz): □ 0.98 (3H, t, J=7.5 Hz), 2.04-2.16 (6H, m), 2.33 (3H, s), 2.79-2.85 (6H, m), 3.49 (2H, 2, J=7.2 Hz), 5.29-5.48 (9H, m), 5.62-5.69 (1H, m). MS (ES): m/z 341 (M+Na)$^+$.

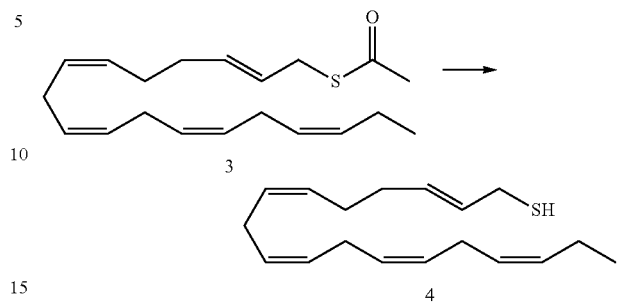

Compound 3 (5.27 g, 16.5 mmol) was dissolved in methanol (50 mL) containing 10 mg □-tocopherol. Potassium carbonate (2.53 g, 18. mmol) was added in one portion at room temperature and the mixture was stirred for 45 minutes under inert atmosphere. The reaction mixture was quenched by way of drop-wise addition of 50 mL 1 M HCl, while cooled on an ice-bath. Subsequently, the mixture was extracted with heptane (3×50 mL), and the combined organic phases washed with brine (50 mL). Drying over Na$_2$SO$_4$ and subsequent filtration and removal of solvent under reduced pressure provided 4.45 g of 4 (97.5% yield) as an orange oil. The crude product was used in the next step without further purification.

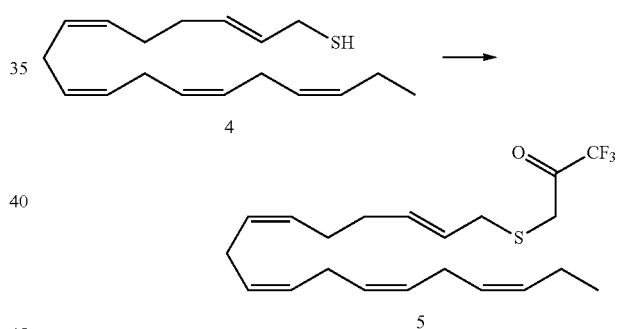

Sodium hydrogen carbonate (2.87 g, 34.2 mmol) was added to thiol 4 (4.45 g, 16.1 mmol), followed by water (50 mL) and ethanol (75 mL). The resulting inhomogeneous mixture was stirred vigorously at room temperature for 20 min under inert atmosphere. 3-Bromo-1,1,1-trifluoroacetone (2.1 ml, 20 mmol) was then added in one portion, and stirring was continued for 45 minutes. The reaction mixture was extracted with n-heptane (2×100 ml). The combined organic phase was washed with brine (50 mL), dried over Na$_2$SO$_4$, filtered and concentrated under reduced pressure. This afforded 6.26 g crude product.

From the crude product, two 2.00 g aliquots were withdrawn and purified further using two different methods.

One aliquot was applied to a 90 g silica column and eluted by way of dry column vacuum chromatography (DCVC, 100 mL fractions, gradient elution n-heptane—100:2 n-heptane:ethyl acetate). Pure fractions were combined and evaporation of solvent under reduced pressure gave 1.64 g of 5 as a pale yellow oil. This corresponds to 82.5% yield for the last step.

A second aliquot was applied to a column with 90 g ODS-AQ stationary phase. Elution was performed by way of DCVC (100 mL fractions, gradient elution 20:80 acetonitrile:water—70:30 acetonitrile:water), and after evaporation of acetonitrile from the fractions containing pure product, the product was extracted back to an organic solvent with 3×100 mL n-heptane. The combined organic extracts were washed with brine (50 mL), dried over $Na_2SO_4$, filtered and concentrated under reduced pressure to give 1.28 g of 5 as a pale orange oil. This corresponds to 64.4% yield for the last step.

Mass and NMR spectral data are similar, except for ratio hydrated/unhydrated in NMR. The given data are for purification method B).

$^1$H NMR (mixture of hydrated/unhydrated), $CDCl_3$, 400 MHz): □ 0.98 (3H, t, J=7.5 Hz), 2.08 (2H, dq, $J_1$=$J_2$=7.4 Hz), 2.12-2-21 (4H, m), 2.76-2.89 (6H, m), 3.10 (0.5H, t, J=7.5 Hz), 3.26 (1.5H, t, J=7.5 Hz), 3.45 (0.5H, s), 3.93 (1.5H, s), 5.28-5.46 (9H, m), 5.56-5.66 (1H, m). MS (ES): m/z 385 (M-H$^+$)$^-$.

The invention claimed is:

1. A process for the preparation of a polyunsaturated ketone comprising:
    (1) reacting a polyunsaturated alcohol in the presence of a compound of formula $R_2$—$SO_2$Hal wherein $R_2$ is a $C_{1-20}$ hydrocarbyl group to form a polyunsaturated sulphonyl ester;
    (2) converting the polyunsaturated sulphonyl ester to a polyunsaturated thioester by reacting with an anion of formula $^-SC(\!=\!O)R_4$ wherein $R_4$ is a $C_{1-20}$ hydrocarbyl group;
    (3) converting the polyunsaturated thioester to form a polyunsaturated thiol optionally in the presence of an antioxidant;
    (4) reacting said polyunsaturated thiol with a compound (LG)$R^3$COX wherein X is an electron withdrawing group, $R^3$ is an alkylene group and LG is a leaving group; optionally in the presence of an antioxidant, so as to form a polyunsaturated ketone compound.

2. A process as claimed in claim 1 comprising:
    (1) reacting a polyunsaturated alcohol of formula (I) or (I')

R—OH or R'—OH     (I) or (I')

wherein R is an optionally substituted $C_{9-23}$ unsaturated hydrocarbon group optionally interrupted by one or more heteroatoms or groups of heteroatoms selected from S, O, N, SO, $SO_2$, said hydrocarbon group comprising at least 2 double bonds; and
    wherein R' is a linear, unsubstituted $C_{9-23}$ unsaturated hydrocarbon group, said hydrocarbon group comprising at least 2 double bonds;
    in the presence of a compound of formula $R_2$—$SO_2$Hal wherein $R_2$ is a $C_{1-20}$ hydrocarbyl group to form a polyunsaturated sulphonyl ester compound of formula (V) or (V')

R-OSO$_2$R$_2$ or R'OSO$_2$R$_2$     (V) or (V')

(2) converting the polyunsaturated sulphonyl ester (V) or (V') to a polyunsaturated thioester by reacting with an anion of formula $^-SC(\!=\!O)R_4$ wherein $R_4$ is a $C_{1-20}$ hydrocarbyl group to form a polyunsaturated thioester compound of formula (VI) or (VI'):

R-SCOR$_4$ or R'—SCOR$_4$     (VI) or (VI')

wherein R and R' are as hereinbefore defined;

(3) converting the polyunsaturated thioester optionally in the presence of an antioxidant and optionally in the presence of a metal carbonate to form a polyunsaturated thiol compound of formula (VII) or (VII')

R—SH or R'—SH     (VII) or (VII')

wherein R and R' are as hereinbefore defined.

3. A process as claimed in claim 2 comprising at least the following steps:
    (1) reacting (3Z,6Z,9Z,12Z,15Z)-octadeca-3,6,9,12,15-pentaen-1-ol

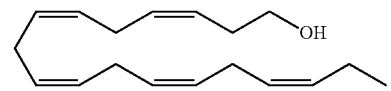 [SMILES: CC/C=C\C/C=C\C/C=C\C/C=C\C/C=C\CCO]

or (2E,6Z,9Z,12Z,15Z,)-octadeca-2,6,9,12,15-pentaen-1-ol;

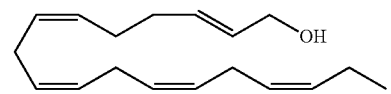 [SMILES: CC/C=C\C/C=C\C/C=C\C/C=C\CC/C=C/CO]

with methanesulphonyl chloride in the presence of a base so as to form a

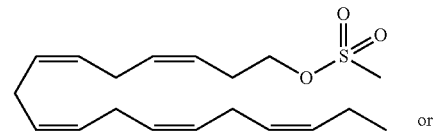

or

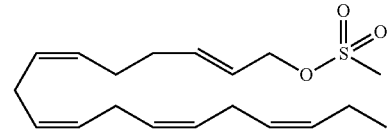

(2) reacting the reaction product of step (1) with a thioacetate ion to form a thioester of formula:

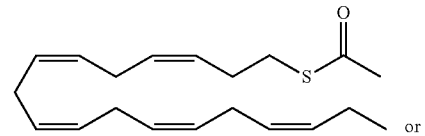

or

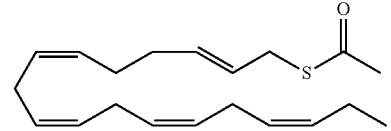

(3) reacting the product of step (2) with potassium carbonate in the presence of an antioxidant to form a thiol of formula:

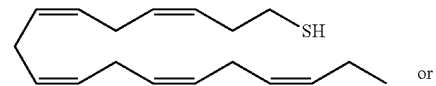

or

-continued

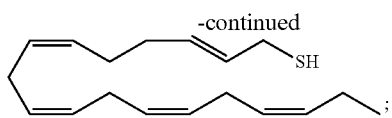

(4) contacting the thiol produced in step (3) with 3-bromo-1,1,1-trifluoroacetone under conditions that produce

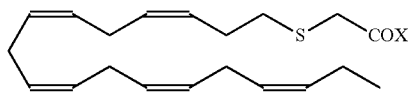

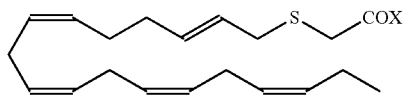

where X is CF$_3$.

4. A process as claimed in claim 2 wherein R is a C$_{11-19}$ linear unsubstituted carbon chain comprising at least 4 non conjugated double bonds.

5. A process as claimed in claim 2 wherein the polyunsaturated alcohol R—OH or R'—OH is obtained by reduction of its corresponding aldehyde R$_1$CHO or R$_1$·CHO in the presence of an electrophilic reducing agent wherein R$_1$ or R$_1$· are as defined for R and R' respectively in which a terminal —CH$_2$— link is removed.

6. A process as claimed in claim 1 wherein the sulphonyl halide is a C$_{1-4}$ alkylsulphonyl chloride.

7. A process as claimed in claim 1 wherein the reaction with the sulphonyl halide takes place in the presence of a base.

8. A process as claimed in claim 1 wherein R$_4$ is a C$_{1-4}$ alkyl so as to form a thioacetate anion.

9. A process as claimed in claim 1 wherein the thiol formation takes place in the presence of a metal carbonate.

10. A process as claimed in claim 1 wherein an antioxidant is present in step (3) and the antioxidant is butyl hydroxyanisole, butyl hydroxytoluene, propyl gallate, tocopherol, ascorbic acid, ascorbyl palmitate, thioglycerol, thioglycolic acid, sodium bisulphite, sodium sulphite, sodium metabisulphite, edetate tetrasodium, or EDTA.

11. A process as claimed in claim 10 wherein the antioxidant is tocopherol.

12. A process as claimed in claim 1 which the product is purified using normal or reversed phase column chromatography.

13. A process as claimed in claim 1 which the polyunsaturated alcohol is purified using normal or reversed phase column chromatography.

14. The process

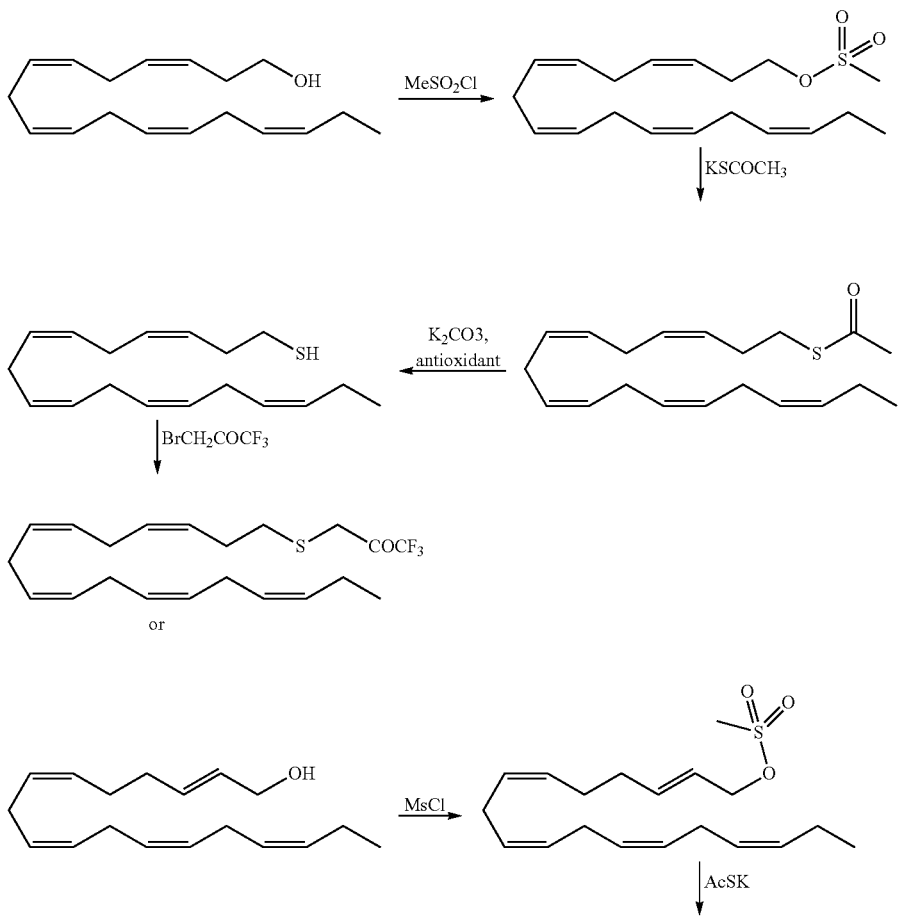

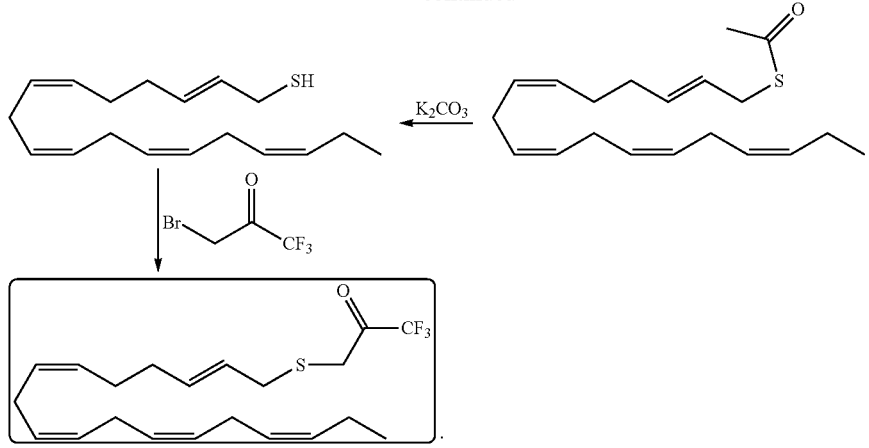

15. A process as claimed in claim 1 wherein $R_2$ is a $C_{1-10}$ alkyl group.

16. A process as claimed in claim 2 wherein R is an optionally substituted $C_{9-23}$ unsaturated hydrocarbon group optionally interrupted by one or more heteroatoms or groups of heteroatoms selected from S, O, N, SO, $SO_2$, said hydrocarbon group comprising at least 4 double bonds; and
    wherein R' is a linear, unsubstituted $C_{9-23}$ unsaturated hydrocarbon group, said hydrocarbon group comprising at least 4 double bonds.

17. A process as claimed in claim 5 wherein the electrophilic reducing agent is DIBAH (diisobutylaluminum hydride).

18. A process as claimed in claim 6 wherein the sulphonyl halide is methanesulphonyl chloride.

19. A process as claimed in claim 7 wherein the base is an amine.

20. A process as claimed in claim 8 wherein $R_4$ is methyl.

21. A process as claimed in claim 20 wherein $R_4$ is methyl so as to form potassium thioacetate.

22. A process as claimed in claim 9 wherein the thiol formation takes place in the presence of potassium carbonate.

23. A process as claimed in claim 11 wherein the antioxidant is o-tocopherol.

24. A process as claimed in claim 1 wherein compound $(LG)R^3COX$ is

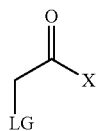

wherein X and LG are as hereinbefore defined.

* * * * *

UNITED STATES PATENT AND TRADEMARK OFFICE
CERTIFICATE OF CORRECTION

PATENT NO. : 10,183,911 B2
APPLICATION NO. : 15/545435
DATED : January 22, 2019
INVENTOR(S) : Marcel Sandberg et al.

It is certified that error appears in the above-identified patent and that said Letters Patent is hereby corrected as shown below:

On the Title Page

Item (12) Delete "Sanderberg et al." and insert --Sandberg et al.--.

Item (72) Delete "Sanderberg" and insert --Sandberg--.

Signed and Sealed this
Fifth Day of May, 2020

Andrei Iancu
*Director of the United States Patent and Trademark Office*